United States Patent
Wang et al.

(10) Patent No.: US 10,274,458 B2
(45) Date of Patent: Apr. 30, 2019

(54) METHOD FOR DETECTING SURFACE COATING PERFORMANCE OF CATHODE ACTIVE MATERIAL

(71) Applicant: Tsinghua University, Beijing (CN)

(72) Inventors: Li Wang, Beijing (CN); Xiang-Ming He, Beijing (CN); Xiao-Ying Pang, Suzhou (CN)

(73) Assignee: TSINGHUA UNIVERSITY, Beijing (CN)

( * ) Notice: Subject to any disclaimer, the term of this patent is extended or adjusted under 35 U.S.C. 154(b) by 0 days.

(21) Appl. No.: 15/954,597

(22) Filed: Apr. 17, 2018

(65) Prior Publication Data
US 2018/0238828 A1 Aug. 23, 2018

Related U.S. Application Data

(63) Continuation of application No. PCT/CN2016/070760, filed on Jan. 13, 2016.

(30) Foreign Application Priority Data

Oct. 30, 2015 (CN) .......................... 2015 1 0724343

(51) Int. Cl.
*H01M 4/02* (2006.01)
*G01N 27/416* (2006.01)
*H01M 4/36* (2006.01)
*H01M 4/48* (2010.01)
*H01M 4/505* (2010.01)
(Continued)

(52) U.S. Cl.
CPC ..... *G01N 27/4167* (2013.01); *G01N 27/4166* (2013.01); *H01M 4/1391* (2013.01);
(Continued)

(58) Field of Classification Search
CPC ....................................................... H01M 4/02
See application file for complete search history.

(56) References Cited

U.S. PATENT DOCUMENTS

2012/0251860 A1* 10/2012 Marple ................ H01M 4/381
429/94
2017/0214043 A1 7/2017 Liu et al.

FOREIGN PATENT DOCUMENTS

| CN | 101949911 A | 1/2011 |
| CN | 103779556 A | 5/2014 |

(Continued)

OTHER PUBLICATIONS

International Search Report of PCT/CN2016/070760.
(Continued)

*Primary Examiner* — Jacob B Marks

(57) ABSTRACT

A method for detecting a surface coating performance of a cathode active material comprising: providing an acid solution with a predetermined concentration; putting a coated cathode active material in a container; adding the acid solution into the container until the coated cathode active material is completely soaked to form a solid liquid mixture; sealing the container, heating and stirring the solid liquid mixture, and recording a series of pH values of a liquid phase of the solid liquid mixture at different points in time; and determining the surface coating performance of the coated cathode active material by comparing the recorded pH values with standard pH values. A method for detecting a surface coating performance of a cathode active material by detecting metal ion concentrations in the solid liquid mixture is also provided.

16 Claims, 4 Drawing Sheets

(51) Int. Cl.
    *H01M 4/525*        (2010.01)
    *H01M 10/0525*      (2010.01)
    *H01M 10/42*        (2006.01)
    *H01M 4/1391*       (2010.01)

(52) U.S. Cl.
    CPC ........... *H01M 4/366* (2013.01); *H01M 4/483* (2013.01); *H01M 4/505* (2013.01); *H01M 4/525* (2013.01); *H01M 10/0525* (2013.01); *H01M 10/4285* (2013.01); *H01M 2004/028* (2013.01)

(56) References Cited

FOREIGN PATENT DOCUMENTS

| | | |
|---|---|---|
| CN | 104282886 A | 1/2015 |
| JP | 2008180693 A | 8/2008 |

OTHER PUBLICATIONS

Li, Jianjun et.al. "Effect of AlPO4 Nano-coating on Electronchemical Property of LiNi1/3Co1/3Mn1/3O2", New Chemical Materials, vol. 41, No. 6, Jun. 2013, SSN:1006-3536, pp. 151-153.

Deng, Sheng-nan et al. "Performance of Li1.2Mn0.54Ni0.13Co0.13O2 as Cathode Materials for Lithium Ion Batteries By Surface Coating" Chinese Journal of Power Sources, vol. 36, No. 4, Apr. 30, 2012,ISSN:1002-087X, pp. 463-466.

Wu, Yingqiang et al. "Coating of Al2O3 on layered Li(Mn1/3Ni1/3Co1/3)O2 Using CO2 as green precipitant and their improved electrochemical performance for lithium ion batteries," Journal of Energy Chemistry, vol. 22, No. 3, May 31, 2013, ISSN: 2095-4956, pp. 468-476.

Li Jiangang et al., Surface reacting of cathode/electrlyte liquid of lithium ion battery, Battery Bimonthly, vol. 34, No. 2, Ari. 2004, pp. 135-137.

* cited by examiner

US 10,274,458 B2

METHOD FOR DETECTING SURFACE COATING PERFORMANCE OF CATHODE ACTIVE MATERIAL

CROSS-REFERENCE TO RELATED APPLICATIONS

This application claims all benefits accruing under 35 U.S.C. § 119 from China Patent Application No. 201510724343.7, filed on Oct. 30, 2015 in the State Intellectual Property Office of China, the content of which is hereby incorporated by reference. This application is a continuation under 35 U.S.C. § 120 of international patent application PCT/CN2016/070760 filed on Jan. 13, 2016, the content of which is also hereby incorporated by reference.

FIELD

The present disclosure relates to methods for detecting surface coating performances of cathode active materials.

BACKGROUND

The chemical and physical stabilities of a cathode active material are key factors affecting the electrochemical performance of a lithium ion battery. Today, developing highly stable cathode active material has been a research focus. When cathode active material is soaked in liquid electrolytes in the battery, the main metal ions in the cathode active material will dissolve easily, migrate away from the cathode and electrochemically deposit on the anode, which influences not only the stability and performance of the cathode active material but also sows the seeds of internal short-circuit. Surface coating of the cathode active material is a conventional method to solve this problem. However, the surface coating performance of the cathode active material is usually indirectly determined through the electrochemical performance test of the cathode or its lithium ion battery. This indirect determination not only takes a long period, but also cannot exclude influence from the lithium ion battery manufacture technology and other materials used in the battery. Therefore, the coating performance of the cathode active material cannot be determined accurately in practical application. A method of directly determining the surface coating performance of the cathode active material is to observe the coated cathode active material under a scanning electron microscope. However, this method is expensive, and only the area under the microscope can be analyzed, which does not objectively reflect the overall coating performance of the cathode active material.

SUMMARY

A low cost, simple, and efficient method for detecting a surface coating performance of a cathode active material is provided.

One embodiment of the method for detecting the surface coating performance of the cathode active material comprises:

S1, providing an acid solution with a predetermined concentration;

S2, putting a coated cathode active material in a container;

S3, adding the acid solution into the container until the coated cathode active material is completely immersed to form a first solid liquid mixture;

S4, sealing the container, heating and stirring the first solid liquid mixture, and recording a series of pH values of a liquid phase of the first solid liquid mixture at different points in time, that is, recorded pH values; and S5, determining the surface coating performance of the coated cathode active material by comparing the recorded pH values with standard pH values.

Another embodiment of the method for detecting the surface coating performance of the cathode active material comprises:

S1, providing an acid solution with a predetermined concentration;

S2, putting a coated cathode active material in a container;

S3, adding the acid solution into the container until the coated cathode active material is immersed completely to form a third solid liquid mixture;

S4, sealing the container, heating and stirring the third solid liquid mixture, and recording a series of metal ion concentrations of liquid phase of the third solid liquid mixture at different points in time, that is, recorded metal ion concentrations; and S5, determining the surface coating performance of the coated cathode active material by comparing the recorded metal ion concentrations with standard metal ion concentrations.

In the present disclosure, the dissolution rate of the metal ion in the cathode active material is reflected by the pH value or the metal ion concentration of the liquid phase of the solid liquid mixture. The surface coating performance of the coated cathode active material can be obtained by comparing the pH values or the metal ion concentrations of the coated cathode active material with that of the standard coated cathode active material. The method in the present disclosure can objectively reflect the overall coating performance on the surface of the cathode active material.

BRIEF DESCRIPTION OF THE DRAWINGS

Implementations are described by way of example only with reference to the attached figures.

DETAILED DESCRIPTION

Figure 1:
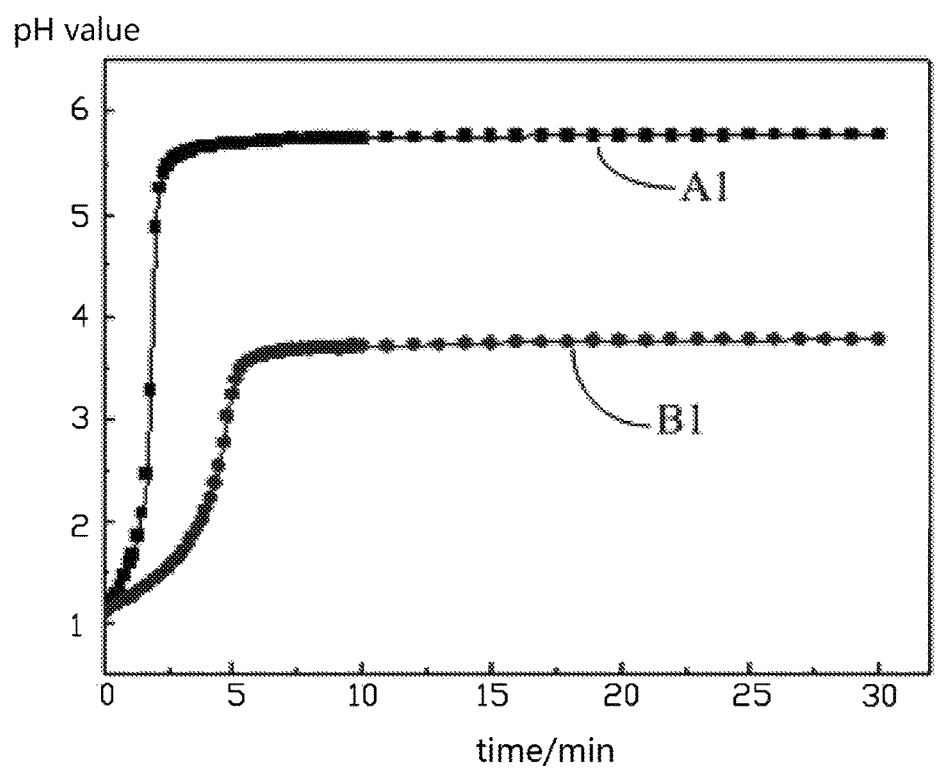
FIG. 1 shows pH value-time curves when an uncoated lithium nickel cobalt manganese oxide ternary cathode active material and a lithium nickel cobalt manganese oxide ternary cathode active material coated with aluminum oxide are respectively reacted with 0.03 mol/L of nitric acid at a temperature of 30° C. according to one embodiment of the present disclosure.

A detailed description with the above drawings is made to further illustrate the present disclosure.

One embodiment of a method for detecting a surface coating performance of a cathode active material includes the following steps of:

S11, providing an acid solution with a predetermined concentration;

S12, putting a coated cathode active material in a container;

S13, adding the acid solution into the container until the coated cathode active material is completely immersed to form a first solid liquid mixture;

S14, sealing the container, heating and stirring the first solid liquid mixture, and recording a series of pH values of a liquid phase of the first solid liquid mixture at different points in time, that is, recorded pH values; and S15, determining the surface coating performance of the coated cathode active material by comparing the recorded pH values with standard pH values.

In S11, the predetermined concentration of the acid solution can be in a range from about 0.01 mol/L to about 0.5 mol/L. The acid solution can be a strong acid, such as hydrochloric acid, nitric acid, or sulfuric acid, or a weak acid, such as acetic acid, oxalic acid, or propionic acid. The predetermined concentration of the acid solution can be measured by a conventional method, such as a pH meter or an acid-base titration method. In one embodiment, a titration method of the acid solution can include the following steps of:

S111, preparing the acid solution;

S112, providing a titrated NaOH solution, slowly dripping the titrated NaOH solution into three samples of the acid solution respectively while detecting the pH value by the pH meter, and stopping the dripping of the titrated NaOH solution when the pH value is 7, calculating three concentrations of the three samples of the acid solution whose relative average deviation should be smaller than 0.2%, and taking an average value of the three concentrations of the three samples of the acid solution as the predetermined concentration of the acid solution.

In S112, the NaOH solution can be titrated by potassium acid phthalate. By using the titrated NaOH solution to titrate the acid solution, an actual concentration of the acid solution can be obtained to ensure that the predetermined concentrations of the acid solutions respectively used in a process of determining the recorded pH values and a process of determining the standard pH values are the same to reduce a pH value error. In one embodiment, the concentration of the acid solution can be in a range from about 0.01 mol/L to about 0.09 mol/L, and the acid solution can be titrated by the NaOH solution with a concentration of 0.01 mol/L. In another embodiment, the concentration of the acid solution can be in a range from about 0.1 mol/L to about 0.5 mol/L, and the acid solution can be titrated by the NaOH solution with a concentration of 0.1 mol/L.

In S13, a solid-liquid ratio of the coated cathode active material and the acid solution is in a range from about 1:1000 to about 1:1. The solid-liquid ratio refers to a volume ratio of the coated cathode active material and the acid solution. The coated cathode active material refers to a cathode active material whose surface is coated with a coating material. The cathode active material can be lithium transition metal oxide, such as at least one of lithium cobalt oxide, lithium manganese oxide, and lithium nickel cobalt manganese oxide ternary cathode active material. The coating material can be various inorganic materials or organic materials, such as one of aluminum oxide, calcium phosphide, and calcium phosphate. In one embodiment, the coating material cannot react with the acid solution.

By immersing the coated cathode active material into the acid solution completely, the coated cathode active material can be in complete contact with the acid solution. A metal ion can be dissolved from the cathode active material in the acid solution, thereby changing the pH value of the acid solution. The coating material can decrease the dissolution of the metal ion, so different surface coating performances can cause different dissolution rates of the metal ion from the cathode active material.

In S14, a probe of the pH meter and a thermometer can be inserted into the first solid liquid mixture. The pH meter is configured to read the pH value of the liquid phase in the first solid liquid mixture in real time which indirectly reflects the dissolution rate of the metal ion from the cathode active material. The thermometer is configured to detect the temperature of the first solid liquid mixture in the detecting process to keep the temperature approximately constant during the heating and stirring. A heating temperature can be in a range from about 0° C. to about 80° C.

The container is sealed to prevent volatilization of the acid solution in the detecting process. The first solid liquid mixture is heated and stirred to ensure the acid solution and the coated cathode active material are fully and uniformly in contact with each other. In one embodiment, the heating method is a water-bath, and the stirring method is at a constant stirring speed. During the heating and stirring, the value shown on the pH meter can be read once at a time interval ranging from about 1 minute to about 150 minutes. The time interval can be determined by the reaction rate of the acid solution and the coated cathode active material.

In the S15, the standard pH values can be a series of comparative reference values which are artificially defined. The determination method of the standard pH values can be substantially the same as S11 to S14, except that the coated cathode active material is substituted with a standard coated cathode active material. In one embodiment, the determination method of the standard pH values includes:

S151, providing the acid solution with the predetermined concentration, wherein the acid solution in the S151 has the same composition and concentration with the acid solution in S11;

S152, putting the standard coated cathode active material into a container;

S153, adding the acid solution into the container until the standard coated cathode active material is completely immersed to form a second solid liquid mixture;

S154, sealing the container, heating and stirring the second solid liquid mixture, and recording a series of standard pH values of a liquid phase of the second solid liquid mixture at different points in time, that is, the standard pH values. A heating temperature in the S154 is the same as the heating temperature in the S14.

The standard pH values are determined by using the standard coated cathode active material to react with the acid solution. The determination process of the standard pH values and the determination process of the recorded pH values can be performed under the same reaction conditions. The same reaction conditions refer to the chemical compositions and the weights of the cathode active materials being the same, the compositions and the concentrations of the acid solutions being the same, and the heating temperatures being the same. In one embodiment, the chemical compositions of the coating materials are same. In one embodiment, the weights of the coating materials are substantially the same. The standard coated cathode active material can be an artificially selected coated cathode active material whose coating performance is determined as qualified, as a standard to evaluate the coating performance. A coating of the coated cathode active material is determined as good, desirable, or favorable when the coating performance is better than the standard, and as bad, undesirable, or unfavorable when the coating performance is worse than the standard. The coating condition on a surface of the standard coated cathode active material can be determined by a scanning electron microscope. In one embodiment, the standard coated cathode active material is a coated cathode active material in which a lithium ion battery can have a high safety, a low self discharge rate, and a high temperature stability.

The standard pH values can include a series of pH values varying with time. The pH value approaches a maximum value as the reaction between the cathode active material and the acid solution progresses. The S15 can further include:

when a maximum value in the recorded pH values is smaller than a maximum value in the standard pH values, determining the dissolution rate of the metal ion in the coated active material as relatively slow and the coating performance of the coated active material as good, otherwise determining the coating performance of the coated active material to be detected as bad; or when a recorded pH value is smaller than a standard pH value at a same point in time, determining the dissolution rate of the metal ion in the coated cathode active material as relatively slow and the coating performance of the coated cathode active material as good, otherwise determining the coating performance of the coated active material as bad; or when a variation rate of the recorded pH values is smaller than a variation rate of the standard pH values, determining the dissolution rate of the metal ion in the coated cathode active material as relatively slow and the coating performance of the coated cathode active material as good, otherwise determining the coating performance of the coated active material to be detected as bad.

Figure 2:
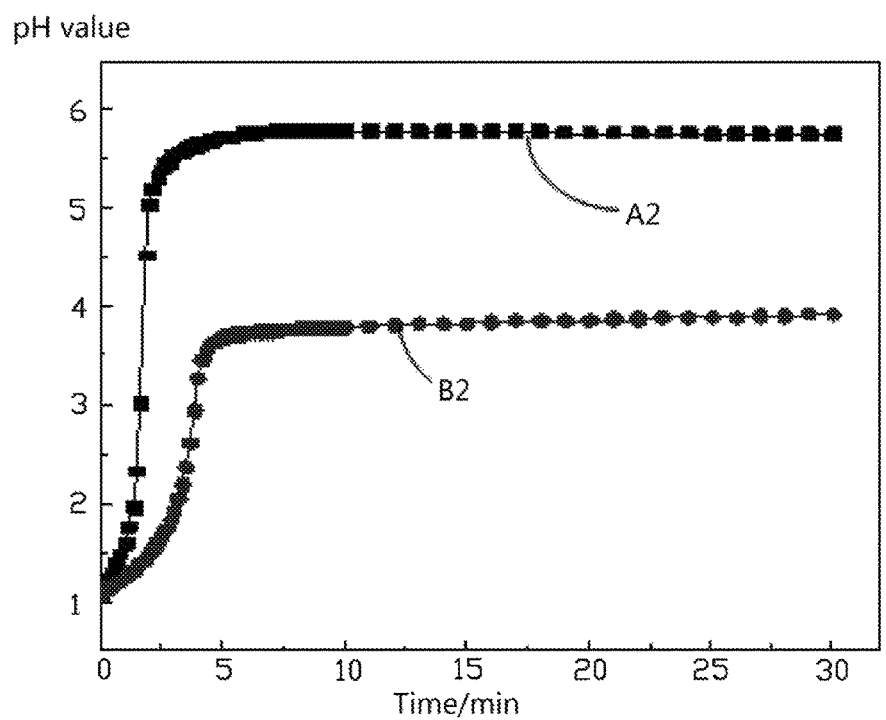
FIG. 2 shows pH value-time curves when the uncoated lithium nickel cobalt manganese oxide ternary cathode active material and the lithium nickel cobalt manganese oxide ternary cathode active material coated with aluminum oxide are respectively reacted with 0.03 mol/L of hydrochloric acid at the temperature of 30° C. according to one embodiment of the present disclosure.
Figure 3:
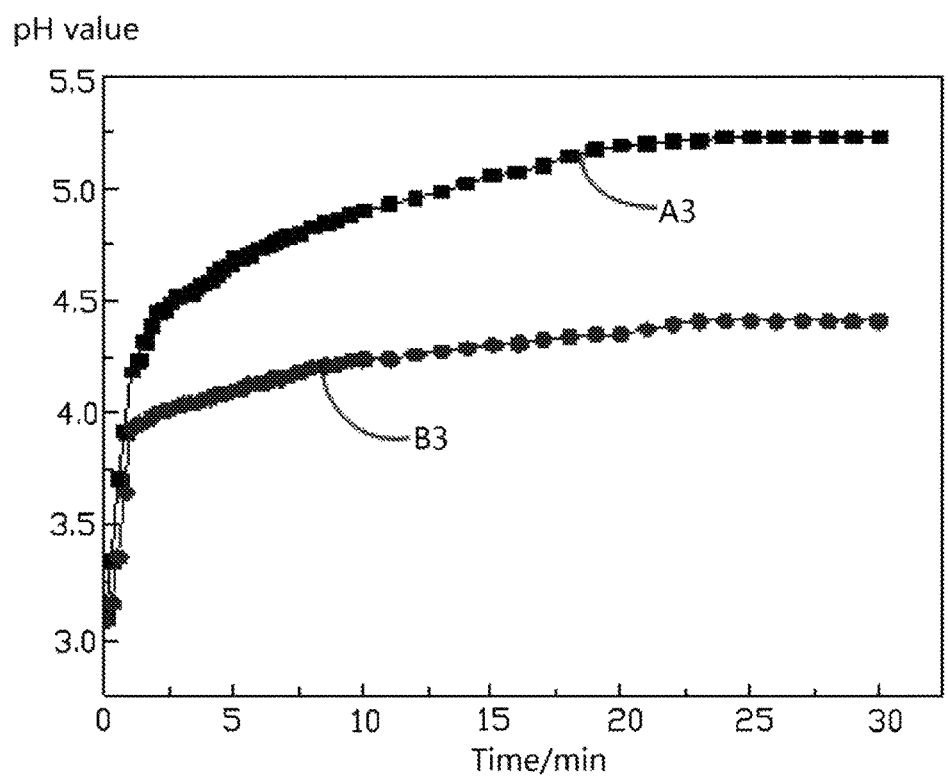
FIG. 3 shows pH value-time curves when the uncoated lithium nickel cobalt manganese oxide ternary cathode active material and the lithium nickel cobalt manganese oxide ternary cathode active material coated with aluminum oxide are respectively reacted with 0.03 mol/L of acetic acid at the temperature of 30° C. according to one embodiment of the present disclosure.

Referring to FIG. 1, FIG. 2 and FIG. 3, A1, A2, and A3 are respectively pH value-time curves when an uncoated lithium nickel cobalt manganese oxide ternary cathode active material is respectively reacted with 0.03 mol/L of nitric acid, hydrochloric acid, and acetic acid at a temperature of 30° C. B1, B2, and B3 are pH value-time curves when a lithium nickel cobalt manganese oxide ternary cathode active material coated with aluminum oxide is respectively reacted with 0.03 mol/L of nitric acid, hydrochloric acid, and acetic acid at the temperature of 30° C. It can be seen that under the same conditions, the pH values of the uncoated lithium nickel cobalt manganese oxide ternary cathode active material and the lithium nickel cobalt manganese oxide ternary cathode active material coated with aluminum oxide at the same point in time are different. At the same point in time, the pH value of the lithium nickel cobalt manganese oxide ternary cathode active material coated with aluminum oxide is smaller than the pH value of the uncoated lithium nickel cobalt manganese oxide ternary cathode active material. Thus, the coating performance can be reflected by the pH value of the liquid phase of the solid liquid mixture, that is, a variation of the pH value of the acid solution can reflect the surface coating performance of the cathode active material.

Example 1

The acid solution in example 1 is acetic acid.

0.4 g of NaOH is weighted and dissolved into 100 mL of deionized water, and then diluted with the deionized water until the volume of the solution is 1000 mL. 2.04 g of potassium acid phthalate is weighted and dissolved into water. The NaOH solution is used to titrate the potassium acid phthalate solution. The standardized NaOH solution is used to titrate the acetic acid to obtain the actual concentration of the acetic acid. 10 g of lithium nickel cobalt manganese oxide ternary cathode active material coated with 1 wt % of aluminum oxide is weighted and added to a three-neck flask. 100 ml of the acetic acid solution with the actual concentration of 0.03 mol/L is added to the three-neck flask to immerse the lithium nickel cobalt manganese oxide ternary cathode active material. The probe of the pH meter and the thermometer are inserted into the three-neck flask, and the three-neck flask is sealed. The solid liquid mixture in the three-neck flask is heated at a temperature of 25° C. by a water bath and stirred with a constant speed, during which the value of the pH meter is recorded every 1 minute to obtain pH values 1. 10 g of lithium nickel cobalt manganese oxide ternary cathode active material coated with 1 wt % of aluminum oxide, which is determined as having a good coating performance by observing under the scanning electron microscope, is weighted and used to repeat the above described procedure, during which the value of the pH meter is recorded every 1 minute to obtain the standard pH values. The pH values 1 are compared to the standard pH values.

Example 2

Example 2 is substantially the same as Example 1, except that 10 g of lithium nickel cobalt manganese oxide ternary cathode active material coated with 1 wt % of aluminum oxide by a different coating method is used. The values of the pH meter are recorded as pH values 2. The pH values 2 are compared to the standard values.

Figure 4:
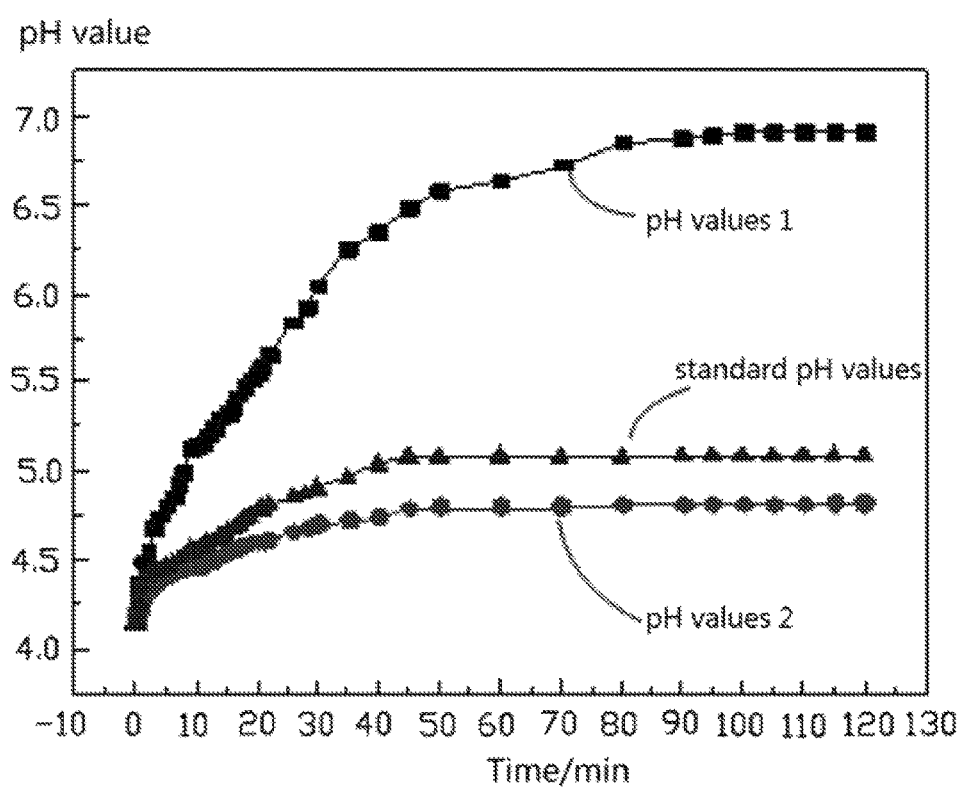
FIG. 4 shows pH value-time curves when two kinds of lithium nickel cobalt manganese oxide ternary cathode active material coated with 1 wt % of aluminum oxide and a standard lithium nickel cobalt manganese oxide ternary cathode active material coated with 1 wt % of aluminum oxide are respectively reacted with acetic acid according to one embodiment of the present disclosure.

Referring to FIG. 4, it can be seen that for the same 10 g of lithium nickel cobalt manganese oxide ternary cathode active material coated with 1 wt % of aluminum oxide, when the coating performances are different, the pH values of the liquid phase of the solid liquid mixture are different. As the reaction time increases, the recorded pH values of Example 1, the recorded pH values of Example 2, and the standard pH values are respectively approaching their maximum values. The maximum pH value of Example 1 is 6.9. The maximum pH value of Example 2 is 4.82. The maximum standard pH value is 5.09. Thus, the coating performance of aluminum oxide in Example 1 is worse than the standard coating performance of aluminum oxide, the coating performance of aluminum oxide in Example 2 is better than the standard coating performance of aluminum oxide, and the coating performance of the 10 g of lithium nickel cobalt manganese oxide ternary cathode active material coated with 1 wt % of aluminum oxide of Example 2 is best.

Another embodiment of the method for detecting the surface coating performance of the cathode active material is provided. The difference between this embodiment with the previous embodiment is that the surface coating performance of the cathode active material is determined by comparing metal ion concentrations in the liquid phase of the solid liquid mixture with standard metal ion concentrations. The metal ion can include at least one of various kinds of metal ions dissolved from the cathode active material in the liquid phase of the solid liquid mixture. The method can include:

S21, providing the acid solution with the predetermined concentration;

S22, putting the coated cathode active material in a container;

S23, adding the acid solution into the container until the coated cathode active material is completely immersed to form a third solid liquid mixture;

S24, sealing the container, heating and stirring the third solid liquid mixture, and recording a series of metal ion concentrations in a liquid phase of the third solid liquid mixture at different points in time, that is, the recorded metal ion concentrations; and S25, judging the surface coating performance of the coated cathode active material by comparing the recorded metal ion concentrations with standard metal ion concentrations.

In S24, the metal ion concentration in the liquid phase of the third solid liquid mixture can be recorded once at a time interval ranging from about 10 minutes to about 150 minutes. The time interval can be determined by the reaction rate of the acid solution and the coated cathode active material. The metal ion concentration in the liquid phase of the third solid liquid mixture can be determined by a conventional method, such as flame atomic absorption spectrophotometer or plasma photoelectric direct-reading spectrophotometer.

In the S25, the standard metal ion concentrations are a series of comparative reference values, which are artificially defined. The determination method of the standard metal ion concentrations is substantially the same as S21 to S24, except that the coated cathode active material is substituted with a standard coated cathode active material. In one embodiment, the determination method of the standard metal ion concentrations includes:

S251, providing the acid solution with the predetermined concentration, wherein the acid solution has the same composition and concentration with the acid solution in the S21;

S252, putting the standard coated cathode active material into a container;

S253, adding the acid solution into the container until the standard coated cathode active material is completely immersed to form a fourth solid liquid mixture;

S254, sealing the container, heating and stirring the fourth solid liquid mixture, and recording a series of metal ion concentrations of a liquid phase of the fourth solid liquid mixture at different points in time, that is, the standard metal ion concentrations. A heating temperature in the S254 is the same as the heating temperature in the S24.

The standard metal ion concentrations are determined by using the standard coated cathode active material to react with the acid solution. The determination process of the standard metal ion concentrations and the determination process of the recorded metal ion concentrations are performed under the same reaction conditions. The same reaction conditions refer to the chemical compositions and the weights of the cathode active materials being the same, the compositions and the concentrations of the acid solutions being the same, and the heating temperatures being the same. In one embodiment, the chemical compositions of the coating materials are the same. In one embodiment, the weights of the coating materials are the same. The standard coated cathode active material can be an artificially selected coated cathode active material whose coating performance is determined as qualified. As a standard to evaluate the coating performance, a coating of the coated cathode active material is determined as good when the coating performance is better than the standard, and to be bad when the coating performance is worse than the standard. The coating situation on a surface of the standard coated cathode active material can be determined by a scanning electron microscope. In one embodiment, the standard coated cathode active material is a coated cathode active material by having which a lithium ion battery can have a high safety, a low self discharge rate, and a good high temperature stability.

The standard metal ion concentrations can include a series of metal ion concentrations varying with time. The metal ion concentrations approach a maximum value as the reaction between the cathode active material and the acid solution progresses. The S25 can further include:

when a maximum value of the recorded metal ion concentrations is smaller than the maximum value of the standard metal ion concentrations, determining the dissolution rate of the metal ions of the coated active material as relatively slow and the coating performance of the coated active material as good, otherwise determining the coating performance of the coated active material as bad; or when a recorded metal ion concentration is smaller than a standard metal ion concentration at a same time point, determining the dissolution rate of the metal ions of the coated active material as relatively slow and the coating performance of the coated active material as good, otherwise determining the coating performance of the coated active material as bad; or when a variation rate of the recorded metal ion concentrations is smaller than a variation rate of the standard metal ion concentrations, determining the dissolution rate of the metal ions of the coated active material as relatively slow and the coating performance of the coated active material as good, otherwise determining the coating performance of the coated active material as bad.

Table 1 shows concentrations of various kinds of metal ions in liquid phases of solid liquid mixtures after respectively immersing an uncoated lithium nickel cobalt manganese oxide ternary cathode active material (NCM) and a lithium nickel cobalt manganese oxide ternary cathode active material coated with aluminum oxide (NCM-$Al_2O_3$) by 0.03 mol/L of nitric acid. Table 2 shows concentrations of various kinds of metal ions in liquid phases of solid liquid mixtures after respectively immersing the uncoated lithium nickel cobalt manganese oxide ternary cathode active material (NCM) and the lithium nickel cobalt manganese oxide ternary cathode active material coated with aluminum oxide (NCM-$Al_2O_3$) by 0.03 mol/L of hydrochloric acid. Table 3 shows concentrations of various kinds of metal ions in liquid phases of solid liquid mixtures after respectively immersing the uncoated lithium nickel cobalt manganese oxide ternary cathode active material (NCM) and the lithium nickel cobalt manganese oxide ternary cathode active material coated with aluminum oxide (NCM-$Al_2O_3$) by 0.03 mol/L of acetic acid. It can be seen that under the same conditions, the concentrations of the same metal ion dissolved respectively from the uncoated lithium nickel cobalt manganese oxide ternary cathode active material and the lithium nickel cobalt manganese oxide ternary cathode active material coated with aluminum oxide at the same point in time point are different, and the concentration of the same metal ion dissolved from the lithium nickel cobalt manganese oxide ternary cathode active material coated with aluminum oxide is smaller than the concentration of the same metal ion dissolved from the uncoated lithium nickel cobalt manganese oxide ternary cathode active material at the same point in time. Thus, the coating performance can be reflected by the concentration of the same metal ion in the liquid phase of the solid liquid mixture, that is, the surface coating performance of the cathode active material can be reflected by a variation of concentrations of the same metal ion in the liquid phase of the solid liquid mixture.

TABLE 1

|  | Content of Li (ppm) | Content of Ni (ppm) | Content of Co (ppm) | Content of Mn (ppm) |
| --- | --- | --- | --- | --- |
| nitric acid immersing NCM | 42.2 | 115.0 | 127.5 | 91.35 |
| nitric acid immersing NCM-$Al_2O_3$ | 33.9 | 68.9 | 77.5 | 88 |

TABLE 2

|  | Content of Li (ppm) | Content of Ni (ppm) | Content of Co (ppm) | Content of Mn (ppm) |
| --- | --- | --- | --- | --- |
| hydrochloric acid immersing NCM | 50.0 | 98.4 | 117.2 | 85.5 |
| hydrochloric acid immersing NCM-$Al_2O_3$ | 36.6 | 77.2 | 80.3 | 72.3 |

TABLE 3

|  | Content of Li (ppm) | Content of Ni (ppm) | Content of Co (ppm) | Content of Mn (ppm) |
| --- | --- | --- | --- | --- |
| acetic acid immersing NCM | 47.1 | 85.7 | 98.3 | 79.2 |
| acetic acid immersing NCM-$Al_2O_3$ | 24.2 | 37.7 | 33.5 | 65.8 |

Example 3

The acid solution of the example 1 is acetic acid.

0.4 g of NaOH is weighted and dissolved into 100 ml of deionized water, and then diluted with the deionized water until the volume of the solution is 1000 mL. 2.04 g of potassium acid phthalate is weighted and dissolved into water. The NaOH solution is used to titrate the potassium acid phthalate solution. The standardized NaOH solution is used to titrate the acetic acid to obtain the actual concentration of the acetic acid. 10 g of lithium nickel cobalt manganese oxide ternary cathode active material coated with 1 wt % of aluminum oxide is weighted and added to a three-neck flask. 100 ml of the acetic acid solution with the actual concentration of 0.03 mol/L is added to the three-neck flask to soak the lithium nickel cobalt manganese oxide ternary cathode active material. The probe of the pH meter and the thermometer are inserted into the three-neck flask and the three-neck flask is sealed. The solid liquid mixture in the three-neck flask is heated at a temperature of 25° C. by a water bath and stirred with a constant speed, and sampled after 120 minutes to detect the concentrations of different metal ions, that is metal ion concentrations of Example 3, by flame atomic absorption spectrometry. 10 g of lithium nickel cobalt manganese oxide ternary cathode active material coated with 1 wt % of aluminum oxide, which is determined as having a good coating performance by observing under the scanning electron microscope, is weighted and used to repeat the above described procedure, and a sample is taken from the solid liquid mixture after 120 minutes to detect the concentrations of different metal ions, that is, standard metal ion concentrations, by flame atomic absorption spectrometry.

Example 4

Example 4 is substantially the same as Example 3, except that 10 g of lithium nickel cobalt manganese oxide ternary cathode active material coated with 1 wt % of aluminum oxide by a different coating method is used. The concentrations of different metal ions in the solid liquid mixture are recorded as metal ion concentrations of Example 4. The metal ion concentrations of Example 4 are compared with the standard metal ion concentrations.

The metal ion concentrations of Example 3, the metal ion concentrations of Example 4, and the standard metal ion concentration are tested and listed in Table 5.

TABLE 5

|  | Content of Li (ppm) | Content of Ni (ppm) | Content of Co (ppm) | Content of Mn (ppm) |
| --- | --- | --- | --- | --- |
| Example 3 | 63 | 224.0 | 256.2 | 185.5 |
| Example 4 | 38.1 | 110.2 | 124.4 | 90.2 |
| Standard metal ion concentrations | 52.7 | 152.3 | 183.5 | 114.2 |

It can be seen from Table 5 that for the same 10 g of lithium nickel cobalt manganese oxide ternary cathode active material coated with 1 wt % of aluminum oxide, when the coating performances are different, the concentrations of the same metal ion in the liquid phase of the solid liquid mixture are different. The concentrations of Li ion, Ni ion, Co ion, and Mn ion of Example 3 are respectively larger than their corresponding standard metal ion concentration, and the coating performance of aluminum oxide in Example 3 is determined as better than the standard coating performance of aluminum oxide. The concentrations of Li ion, Ni ion, Co ion, and Mn ion of Example 4 are respectively smaller than their corresponding standard metal ion concentration, and the coating performance of aluminum oxide in Example 4 is judged as worse than the standard coating performance of aluminum oxide.

In the present disclosure, the surface coating performance of the cathode active material can be determined according to the pH value or the concentrations of various kinds of metal ion of a solution obtained after the acid solution is reacted with the coated cathode active material. The method is low cost, simple, and efficient. The method can meet demands of research and production, and can be configured to detect the surface coating performance of various cathode active materials.

Finally, it is to be understood that the above-described embodiments are intended to illustrate rather than limit the present disclosure. Variations may be made to the embodiments without departing from the spirit of the present disclosure as claimed. Elements associated with any of the above embodiments are envisioned to be associated with any other embodiments. The above-described embodiments illustrate the scope of the present disclosure but do not restrict the scope of the present disclosure.

What is claimed is:

1. A method for detecting a surface coating performance of a cathode active material, the method comprising:
   S11, providing an acid solution with a predetermined concentration;
   S12, putting a coated cathode active material in a first container;
   S13, adding the acid solution into the first container until the coated cathode active material is immersed to form a first solid liquid mixture;
   S14, sealing the first container, heating and stirring the first solid liquid mixture, and recording a series of pH values of a liquid phase of the first solid liquid mixture at different points in time; and
   S15, determining the surface coating performance of the coated cathode active material by comparing the recorded pH values with standard pH values.

2. The method of claim 1, wherein the predetermined concentration of the acid solution is in a range from about 0.01 mol/L to about 0.5 mol/L.

3. The method of claim 1, wherein a volume ratio of the coated cathode active material to the acid solution in the first solid liquid mixture is in a range from about 1:1000 to about 1:1.

4. The method of claim 1, wherein a temperature of the first solid liquid mixture is approximately constant during the heating and stirring.

5. The method of claim 1, wherein the standard pH values is determined by:
   S151, providing the acid solution with the predetermined concentration;
   S152, putting a standard coated cathode active material in a second container;
   S153, adding the acid solution into the second container until the standard coated cathode active material is immersed to form a second solid liquid mixture; and
   S154, sealing the second container, heating and stirring the second solid liquid mixture, and recording a series of standard pH values of liquid phase of the second solid liquid mixture at the different points in time.

6. The method of claim 5, wherein the standard coated cathode active material has a qualified surface coating performance.

7. The method of claim 1, wherein S15 further comprises:
   when a maximum value of the recorded pH values is smaller than a maximum value of the standard pH values, determining the surface coating performance of the coated active material as favorable, otherwise determining the surface coating performance of the coated active material as unfavorable; or
   when a recorded pH value is smaller than a standard pH value at a same point in time, determining the surface coating performance of the coated active material as favorable, otherwise determining the surface coating performance of the coated active material as unfavorable; or
   when a variation rate of the recorded pH values is smaller than a variation rate of the standard pH values, determining the surface coating performance of the coated active material as favorable, otherwise determining the surface coating performance of the coated active material as unfavorable.

8. The method of claim 1, wherein the acid solution is selected from the group consisting of hydrochloric acid, nitric acid, sulfuric acid, acetic acid, oxalic acid, propionic acid, and combinations thereof.

9. A method for detecting a surface coating performance of a cathode active material comprising:
   S21, providing an acid solution with a predetermined concentration;
   S22, putting a coated cathode active material in a third container;
   S23, adding the acid solution into the third container until the coated cathode active material is immersed to form a third solid liquid mixture;
   S24, sealing the container, heating and stirring the third solid liquid mixture, and recording a series of metal ion concentrations in liquid phase of the third solid liquid mixture at different points in time; and
   S25, determining the surface coating performance of the coated cathode active material by comparing the recorded metal ion concentrations with standard metal ion concentrations.

10. The method of claim 9, wherein the predetermined concentration of the acid solution is in a range from about 0.01 mol/L to about 0.5 mol/L.

11. The method of claim 9, wherein a volume ratio of the coated cathode active material to the acid solution in the third solid liquid mixture is in a range from about 1:1000 to about 1:1.

12. The method of claim 9, wherein a temperature of the third solid liquid mixture is approximately constant during the heating and stirring.

13. The method of claim 9, wherein the standard metal ion concentrations is determined by:
   S251, providing the acid solution with the predetermined concentration;
   S252, putting a standard coated cathode active material in a fourth container;
   S253, adding the acid solution into the fourth container until the standard coated cathode active material is immersed to form a fourth solid liquid mixture; and
   S254, sealing the second container, heating and stirring the fourth solid liquid mixture, and recording a series of standard metal ion concentrations of liquid phase of the fourth solid liquid mixture at the different points in time.

14. The method of claim 13, wherein the standard coated cathode active material has a qualified surface coating performance.

15. The method of claim 9, wherein the S25 further comprises:
   when a maximum value of the recorded metal ion concentrations is smaller than a maximum value of the standard metal ion concentrations, determining the surface coating performance of the coated active material as favorable, otherwise judging the surface coating performance of the coated active material as unfavorable; or
   when a recorded metal ion concentration is smaller than a standard metal ion concentration at a same point in time, judging the surface coating performance of the coated active material as favorable, otherwise judging the surface coating performance of the coated active material as unfavorable; or
   when a variation rate of the recorded metal ion concentrations is smaller than a variation rate of the standard metal ion concentrations, determining the surface coating performance of the coated active material as favorable, otherwise determining the surface coating performance of the coated active material as unfavorable.

16. The method of claim 9, wherein the acid solution is selected from the group consisting of hydrochloric acid, nitric acid, sulfuric acid, acetic acid, oxalic acid, propionic acid, and combinations thereof.

\* \* \* \* \*